(12) United States Patent
Friedemann

(10) Patent No.: US 8,502,047 B1
(45) Date of Patent: Aug. 6, 2013

(54) HYBRID CORN VARIETY 980001

(75) Inventor: Peter D. Friedemann, Philo, IL (US)

(73) Assignee: Agrigenetics, Inc., Indianapolis, IN (US)

( * ) Notice: Subject to any disclaimer, the term of this patent is extended or adjusted under 35 U.S.C. 154(b) by 197 days.

(21) Appl. No.: 13/089,342

(22) Filed: Apr. 19, 2011

Related U.S. Application Data

(60) Provisional application No. 61/326,689, filed on Apr. 22, 2010.

(51) Int. Cl.
*A01H 5/00* (2006.01)
*A01H 1/00* (2006.01)
*A01H 5/10* (2006.01)
*C12N 15/82* (2006.01)

(52) U.S. Cl.
USPC ........ 800/320.1; 800/301; 800/302; 800/275; 800/265; 800/264; 800/278; 800/279; 800/281; 435/412

(58) Field of Classification Search
None
See application file for complete search history.

(56) References Cited

U.S. PATENT DOCUMENTS

| | | | |
|---|---|---|---|
| 5,523,520 A | 6/1996 | Hunsperger et al. | |
| 6,025,547 A | 2/2000 | Stucker | |
| 6,096,953 A | 8/2000 | Hoffbeck | |
| 7,875,780 B1 * | 1/2011 | Byrnes et al. | 800/320.1 |

OTHER PUBLICATIONS

Allard, In Principles of Plant Breeding, John Wiley & Sons, Inc. pp. 155-156, 1960.
Phillips, et al., In Corn and Corn Improvement, ASA Monograph No. 18, 3rd edition, pp. 345, 358, 1988.
Eshed, et al., Genetics (1996), vol. 143, pp. 1807-1817.
Kraft, et al., Theoretical Applied Genetics (2000), vol. 101, pp. 323-326.
Murray, et al., Proceedings of the 43rd Annual Corn and Sorghum Industry Research Conference, vol. 43, p. 72-87, 1988.

* cited by examiner

*Primary Examiner* — Stuart F Baum
(74) *Attorney, Agent, or Firm* — Eric J. Kraus; TraskBritt, P.C.

(57) ABSTRACT

The invention provides seed and plants of the hybrid corn variety designated 980001. The invention thus relates to the plants, seeds and tissue cultures of the variety 980001, and to methods for producing a corn plant produced by crossing a corn plant of variety 980001 with itself or with another corn plant, such as a plant of another variety. The invention further relates to genetic complements of plants of variety 980001.

20 Claims, No Drawings

HYBRID CORN VARIETY 980001

This application claims a priority based on provisional application 61/326,689 which was filed in the U.S. Patent and Trademark Office on Apr. 22, 2010, the entire disclosure of which is hereby incorporated by reference.

FIELD OF THE INVENTION

This invention is in the field of corn breeding. In particular, the invention relates to a hybrid corn variety designated 980001 that include plants and seeds of hybrid corn variety.

BACKGROUND OF THE INVENTION

Corn (*Zea mays* L.) is the most important and abundant crop produced in the United States. Corn is used as human food, livestock feed, and as an industrial raw material. The food uses of corn include kernels for human consumption, dry milling products such as grits, meal and flour, and wet milling products such as corn starch, corn syrups, and dextrose. Corn oil recovered from corn germ is a by-product of both dry and wet milling industries. Both grain and non-grain portions of corn plants are used extensively as livestock feed, primarily for beef cattle, dairy cattle, hogs, and poultry.

Corn is used to produce ethanol while corn starch and flour are used in the paper and textile industries. Corn is also used in adhesives, building materials, foundry binders, laundry starches, explosives, oil-well muds, and other mining applications. Plant parts other than the grain of corn are also used in industry; for example, stalks and husks are made into paper and wallboard and cobs are used for fuel and to make charcoal.

The goal of a corn breeder is to improve a corn plant's performance and therefore, its economic value by combining various desirable traits into a single plant. Improved performance is manifested in many ways. Higher yields of corn plants contribute to a more abundant food supply, a more profitable agriculture and a lower cost of food products for the consumer. Improved quality makes corn kernels more nutritious. Improved plant health increases the yield and quality of the plant and reduces the need for application of protective chemicals. Adapting corn plants to a wider range of production areas achieves improved yield and vegetative growth. Improved plant uniformity enhances the farmer's ability to mechanically harvest corn.

Natural, or open pollination, occurs in corn when wind blows pollen from the tassels to the silks that protrude from the tops of the ear shoot and may include both self- and cross-pollination. Vigor is restored when two different inbred lines are cross-pollinated to produce the first generation ($F_1$) progeny. A cross between two defined homozygous inbred corn plants produce a uniform population of heterozygous hybrid corn plants and such hybrid corn plants are capable of being generated indefinitely from the corresponding inbred seed supply.

When two different, unrelated inbred corn parent plants are crossed to produce an $F_1$ hybrid, one inbred parent is designated as the male, or pollen parent, and the other inbred parent is designated as the female, or seed parent. Because corn plants are monoecious, hybrid seed production requires elimination or inactivation of pollen produced by the female parent to render the female parent plant male sterile. This serves to prevent the inbred corn plant designated as the female from self-pollinating.

The development of hybrid corn plants is a slow, costly process that requires the expertise of breeders and many other specialists. The development of new hybrid corn varieties in a corn plant breeding program involves numerous steps, including: (1) selection of parent corn plants (germplasm) for initial breeding crosses; (2) inbreeding of the selected plants from the breeding crosses for several generations to produce a series of inbred lines, which individually breed true and are highly uniform; and, (3) crossing a selected inbred line with an unrelated line to produce the $F_1$ hybrid progeny having restored vigor.

Because hybrid corn varieties lose their commercial competitiveness over time, a continuing need exists for novel hybrid corn varieties with improved characteristics. The present invention exhibits high digestibility and high tonnage for its maturity compared to other BM3 hybrids and standard industry silage hybrids of similar maturity. To protect and to enhance yield production, trait technologies and seed treatment options provide additional crop plan flexibility and cost effective control against insects, weeds and diseases, thereby further enhancing the potential of hybrid corn variety 980001.

DETAILED DESCRIPTION OF THE INVENTION

I. Definitions of Plant Characteristics

In the description and examples that follow, a number of terms are used. To provide a clear and consistent understanding of the specification and claims, including the scope to be given such terms, the following definitions are provided.

Anther Color: Recorded at the time of pollen shed when anthers are actively dehiscing pollen as a standard color name and Munsell color code.

Anthocyanin in Brace Roots: This is a relative rating of the expression of anthocyanin in the brace roots (1=none, 2=faint, 3=50% purpling/moderate, and 4=dark) recorded two weeks after flowering.

Aphid Attractiveness: This represents the relative level of aphid numbers found on an emerging tassel up to and during the period of pollen shed rated as high, average or none.

Cob Color: Recorded as a standard color name and Munsell color code.

% Starch: This represents the percent amylose and amylopectin content on a dry matter basis of chopped silage.

Ears Per Stalk: The total number of ears with seed set on each plant.

Ear Height: This is the distance in centimeters from the ground to the highest placed ear node point of attachment of the ear shank of the uppermost developed ear on the stalk.

Ear Leaves: Ear leaves are defined as one or more distinct ear leaves on ear husks at flowering (usually >0.25 to 0.5") represented as present or absent. This characteristic may be difficult to determine, may be environmentally influenced, and is not recorded as present unless the ear leaves are present in sufficient size or on several plants in the middle of the row.

Ear Length: This is the length of an unhusked ear from the butt to the tip in centimeters.

Ear Position At Dry Husk: This represents the relative direction of the top ear observed 65 days after pollinating while still attached to the plant rated as 1=upright, 2=horizontal and 3=pendent Ear Taper: This represents the relative taper of the unshelled ear rated as slight or nearly straight (1), average (2), or extreme or conical (3).

Endosperm Type: Endosperm is the material in the region of the kernel between the germ and the seed coat and is rated on the following scale: 1=sweet, 2=extra sweet (sh2), 3=normal starch, 4=high amylase starch, 5=waxy, 6=high protein, 7=high lysine, 8=supersweet (se), 9=high oil and 10=other-specify.

Environments: This is the number of different geographic locations where two hybrids are grown together and in the same experiment.

50% Pollen (GDU from Planting): The number of GDUs after planting when 50% of the plants are shedding pollen.

50% Silk (GDU from Planting): The number of GDUs after emergence when 50% of the plants have extruded silk.

GDU: Growing degree unit(s) is a measure of the number of GDUs or heat units used in the tracking of flowering and maturation of inbred lines and hybrid. Growing degree units are calculated using the Barger Method, wherein the heat units for a 24-hour period are represented by the formula: [(Max. temp+MM. temp)/2]−50 and the highest maximum temperature used is 86° F. and the lowest minimum temperature used is 50° F.

Genotype: Refers to the genetic constitution of a corn plant or cell.

Glume Band: Recorded as absent or, if present, as a standard color name and Munsell color code.

Glume Color: Recorded after exposure to sunlight and just before extruding anthers as a standard color name and Munsell color code.

Hard Endosperm Color: This is the color of the region of the endosperm between the floury endosperm and the aleurone layer in yellow dent corn recorded as a standard color name and a Munsell color code.

Husk Tightness: This represents the relative ability for husks to be removed either manually or through commercial production husking beds 65 days after flowering rated as loose (2), average (5) and 8 (tight).

Kernel Crown Color: This is the color of the portion of the kernel distal to the tip cap recorded as a standard color name and Munsell color code.

K Row Alignment: This is kernel row alignment and is scored as straight, slightly curved or spiral determined by standing the unshelled ear on its base and looking down at the tip.

Kernel Rows: The presence (distinct) or absence (indistinct) of defined kernel rows.

Lateral Tassel Branches: This represents the number of primary lateral tassel branches that originate from the central spike.

Leaf Color: Recorded as standard color name and Munsell color code.

Moisture: Actual percentage moisture of the grain at harvest.

Munsell Code: This refers to a standard color reference, the Munsell Color Chart for Plant Tissues.

NDFD: This is the percent of neutral detergent fiber digestability measured in vitro.

Number of Kernel Rows: This is the average total number of kernel rows on the ear. If the rows are indistinct, then this value is an average number of kernels located around the circumference of the ear at the mid-point of its length.

Number of Leaves Above Ear: This represents the average number of leaves above the ear leaf.

Phenotype: Refers to the physical or external appearance of a corn plant.

Plant Height: This is the plant height in centimeters from the ground to the tip of the tassel.

Population: This is the planting density on a per acre basis.

Root Lodging: This is the percentage of corn plants that root lodge, i.e., those plants that lean from the vertical axis at an approximate 30° angle or greater just before anthesis.

Silk Color: Recorded 3 days after emergence using standard color name and Munsell color code.

Stalk Lodging: This is the percentage of corn plants that stalk lodge, i.e., those plants that are broken over, at or below the top ear node at harvest.

Standard Color Names: These color names include light green, medium green, dark green, very dark green, green-yellow, pale yellow, yellow, yellow orange, salmon, pink-orange, pink, light red, cherry red, red, red and white, pale purple, purple, colorless, white, white capped, buff, tan, brown, bronze and variegated.

Tassel Length: This is the length of the tassel from the top leaf collar to the tassel tip measured in centimeters.

Tassel Type: This is the tassel branch shape recorded as erect or spreading. The angle of the base of each tassel branch is used to indicate the direction of the branches. Erect longer or lighter tassels that droop over on the tip are classified as erect.

Tons/Acre: This represents the amount in tons of all harvested above ground plant material per acre adjusted to 65% silage moisture.

Years: This refers to the number of calendar years included in a comparison.

II. Hybrid Corn Variety 980001

A. Hybrid Corn Variety 980001

In accordance with one aspect of the present invention, provided is a new yellow dent hybrid corn variety and plants thereof designated 980001. Hybrid variety 980001 was produced from a cross of the inbred varieties designated BE1146BMR and LLD06BM. The inbred parents have been self-pollinated and ear-rowed a sufficient number of generations with careful attention paid to uniformity of plant type to show uniformity and stability within the limits of environmental influence. A description of physiological and morphological characteristics of hybrid corn variety 980001 is presented in Table 1. It should be noted that these characteristics may have been measured on a trait bearing version of hybrid corn variety 980001. However, one of ordinary skill in corn breeding art would recognize that the measured characteristics would be representative of either the non-trait bearing version or a trait-bearing versions.

| Corn Hybrid 980001 Phenotypic Descriptions Character | |
|---|---|
| 50% of plants shedding pollen(GDU) | 1430 |
| 50% of Plants silking (GDU) | 1458 |
| Anther Color (Std chart color) | 1 (Light Green) |
| Anther Color (Munsell Code) | 2.5R 8/4 |
| Glume Color (Std chart color) | 1 (Light Green) |
| Glume Color (Munsell Code) | 2.5GY 8/4 |
| Silk Color (Std Color Name) | 5 (Green-Yellow) |
| Silk Color (Munsell Code) | 2.5GY 8/10 |
| Glume Band (Pr/Abs) | Abs |
| Attractive to Aphids (H, Av, N) | None |
| Plant Ht (to tassel tip - cm) | 271 |
| Ear Ht (top ear node - cm) | 141 |
| Ear Leaves (Pr/Abs) | Abs |
| Anthocyanin in brace roots (rating) | 3 |
| Leaf Color (Std) | 3 (Dark Green) |
| Leaf Color (Munsell Code) | 5GY 5/8 |
| # Leaves Above Ear | 7 |
| Tassel Length (cm) | 41 |
| # Tassel Branches - Lateral | 5 |
| # Ears Per Stalk | 1 |
| Position of Ear at Dry Husk (rating) | 2 |
| Husk Tightness (rating) | 2 |

-continued

| Corn Hybrid 980001 Phenotypic Descriptions Character | |
|---|---|
| Ear Length (cm) | 21 |
| # Kernel Rows | 18 |
| Kernel Rows (1 = distinct, 2 = indistinct) | 1 |
| Kernel Row Alignment | 3 |
| Ear Taper (1-slight, 2-average, 3 extreme) | 2 |
| EndosPerm type (1-10 rating, see pg 3) | 3 |
| Cob Color (std) | 14 (Red) |
| Cob Color (Munsell code) | 2.5YR 5/8 |
| Hard Endosperm (Std Color) | 8 (Yellow-Orange) |
| Hard Endosperm (MunSell Code) | 7.5YR 6/10 |
| Kernel Crown Color (std) | 7 (Yellow) |
| Kernel Crown Color (Munsell) | 2.5Y 8/10 |
| Tassel Type | Spreading |

It should be appreciated by one having ordinary skill in the art that, for the quantitative characteristics identified in Table 1, the values presented are typical values. These values may vary due to the environment and accordingly, other values that are substantially equivalent are also within the scope of the invention.

The present invention also relates to one or more corn plant parts of hybrid corn variety 980001. Corn plant parts include plant cells, plant protoplasts, plant cell tissue cultures from which corn plants can be regenerated, plant DNA, plant calli, plant clumps, and plant cells that are intact in plants or parts of plants, such as embryos, pollen, ovules, flowers, seeds, kernels, ears, cobs, leaves, husks, stalks, roots, root tips, brace roots, lateral tassel branches, anthers, tassels, glumes, silks, tillers, and the like.

B. Hybrid Corn Variety Seed Designated 980001

A corn kernel is composed of four structural parts: (1) the pericarp, which is a protective outer covering (also known as bran or hull); (2) the germ (also known as an embryo); (3) the endosperm; and, (4) the tip cap, which is the point of attachment to the cob. Another aspect of the present invention is one or more parts of hybrid corn variety seed 980001, such as the pericarp or the germ and/or the endosperm which remain upon removal of the pericarp and adhering remnants of the seed coat.

Corn yield is affected by the conditions to which seeds and seedlings (young plants grown from seeds) are exposed. Seeds and seedlings may be exposed to one of, or a combination of, for example, cold, drought, salt, heat, pollutants, and disease, all of which are conditions that potentially retard or prevent the growth of crops therefrom. For example, temperature extremes are typical in the upper Midwest region of the United States. Furthermore, diseases evolved from pathogens and deterioration caused by fungi are potentially harmful to seeds and seedlings. Thus, it is desirable to treat seeds as by coating or impregnating the seeds with compositions that render the seeds and seedlings grown therefrom more hardy when exposed to such adverse conditions.

Accordingly, another aspect of the present invention relates to a coated and/or impregnated seed of hybrid corn variety designated 980001 and to coated and/or impregnated seed derived therefrom. Various agents have been used to treat seeds to increase resistance of the plants to stressed conditions, such as cold, drought, salt, and fungi. Such agents include, for example, sodium methylphenyl-pentadienate, trichloroacetic acid, polyoxyalkylene-organo-siloxane block copolymer, 5-aminolevulinic acid, salicylic acid, thiamethoxam, potassium chloride, and polyvinyl alcohol and are useful alone, or in combination in the present invention.

C. Deposit Information

A deposit of at least 2500 seeds of inbred parent plant varieties BE1146BMR (U.S. application Set. No. 10/678,735, filed Oct. 3, 2003, the entire disclosure of which is incorporated herein by reference) and LLD06BM (U.S. application Ser. No. 12/131,306, filed Jun. 2, 2008, the entire disclosure of which is incorporated herein by reference) has been made with the American Type Culture Collection (ATCC), 10801 University Boulevard, Manassas, Va. 20110-2209 USA, and assigned ATCC Accession Nos. PTA-5448, and PTA-8519, respectively. The seeds were deposited with the ATCC on Sep. 3, 2003, and Jun. 28, 2007, respectively. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et sea.).

III. Processes of Preparing Novel Corn Plants

A. Novel Inbred Plants Obtained From Hybrid Corn Variety 980001

In accordance with processes of the present invention, hybrid corn variety 980001 is crossed with itself or any different corn plant such as an inbred corn plant or a hybrid corn plant to develop a novel inbred line. For example, hybrid corn variety 980001 may be inbred, i.e., crossed to itself or sib-pollinated, and the resulting progeny each selfed for about 5 to about 7 or more generations, thereby providing a set of distinct, pure-breeding inbred lines wherein each of the lines received all of its alleles from the hybrid corn plant. Double haploid methods can also be used to obtain an inbred corn plant that is homozygous at essentially every locus, wherein the inbred corn plant received all of its alleles from the hybrid corn plant. In other embodiments, hybrid corn variety 980001 is crossed with a different corn plant that may include any inbred corn plant, another germplasm source, a haploid or mutation inducing stock, or a trait donor plant, thereby providing a set of distinct, pure-breeding inbred lines. The resulting inbred lines could then be crossed with other inbred or non-inbred lines and the resulting inbred progeny analyzed for beneficial characteristics. In this way, novel inbred lines conferring desirable characteristics could be identified.

IV. Novel Hybrid Plants

A. Novel Hybrid Seeds and Plants

In yet another aspect of the invention, processes are provided for producing hybrid corn variety 980001, which processes generally comprise crossing a first parent corn plant BE1146BM with a second parent corn plant LLD06BM. In these processes, crossing will result in the production of seed. The seed production occurs regardless whether the seed is collected.

Any time the inbred corn plant BE1146BM is crossed with another, different corn inbred plant LLD06BM, a first generation ($F_1$) corn hybrid variety 980001 plant is produced. Therefore, any $F_1$ hybrid corn plant or corn seed which is produced with these two parent corn lines is part of the present invention.

In embodiments of the present invention, the first step of "crossing" the first and the second parent corn plants comprises planting, preferably in pollinating proximity, seeds of a first inbred corn plant and a second, distinct inbred corn plant. As discussed herein, the seeds of the first inbred corn plant and/or the second inbred corn plant can be treated with compositions that render the seeds and seedlings grown therefrom more hardy when exposed to adverse conditions.

A further step comprises cultivating or growing the seeds of the first and second parent corn plants into plants that bear flowers. If the parental plants differ in timing of sexual maturity, techniques may be employed to obtain an appropriate nick, i.e., to ensure the availability of pollen from the parent corn plant designated the male during the time at which silks on the parent corn plant designated the female are receptive to the pollen. Methods that may be employed to obtain the desired nick include delaying the flowering of the faster maturing plant, such as, but not limited to delaying the planting of the faster maturing seed, cutting or burning the top leaves of the faster maturing plant (without killing the plant) or speeding up the flowering of the slower maturing plant, such as by covering the slower maturing plant with film designed to speed germination and growth or by cutting the tip of a young ear shoot to expose silk.

In a preferred embodiment, the corn plants are treated with one or more agricultural chemicals as considered appropriate by the grower.

A subsequent step comprises preventing self-pollination or sib-pollination of the plants, i.e., preventing the silks of a plant from being fertilized by any plant of the same variety, including the same plant. This is preferably done in large scale production by controlling the male fertility, e.g., treating the flowers so as to prevent pollen production or alternatively, using as the female parent a male sterile plant of the first or second parent corn plant (i.e., treating or manipulating the flowers so as to prevent pollen production, to produce an emasculated parent corn plant or using as a female, a cytoplasmic male sterile version of the corn plant). This control may also be accomplished in large scale production by physical removal of the tassel from the female plant, either by pulling the tassel by hand, cutting with a rotary cutter, or pulling with a mechanical tassel pulling machine. In small scale production, corn breeder's shoot bags, usually plastic or glassine, applied to cover the ear shoot prior to the extrusion of silks provide effective control of unwanted self-pollination or sib-pollination.

Yet another step comprises allowing cross-pollination to occur between the first and second parent corn plants. When the plants are not in pollinating proximity, this is done by placing a bag, usually paper, over the tassels of the first plant and another shoot bag over the ear shoot, prior to the extrusion of silk, of the incipient ear on the second plant. The bags are left in place usually overnight. Since pollen stops shedding each day and loses viability and new pollen is shed each morning, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels and removed from the first plant. Finally, in one continuous motion, the shoot bag is removed from the silks of the incipient ear on the second plant, and the pollen bag containing the captured pollen is placed over the silks of the incipient ear of the second plant, shaken again to disperse the captured pollen, and left in place covering the developing ear to prevent contamination from any unwanted fresh airborne pollen. In large scale production, crossing is accomplished by isolated open-pollinated crossing fields whereby corn plants of the parent designated as the female, which are controlled for male fertility, are allowed to be pollinated by other plants of a different corn type where such plants are adjacent to the plants designated as the female parent.

A further step comprises harvesting the seeds, near or at maturity, from the ear of the plant that received the pollen. In a particular embodiment, seed is harvested from the female parent plant, and when desired, the harvested seed can be grown to produce a first generation ($F_1$) hybrid corn plant.

Yet another step comprises drying and conditioning the seeds, including the treating, sizing (or grading) of seeds, and packaging for sale to growers for the production of grain or forage. As with inbred seed, it may be desirable to treat hybrid seeds with compositions that render the seeds and seedlings grown therefrom more hardy when exposed to adverse conditions. Mention should be made that resulting hybrid seed is sold to growers for the production of grain and forage and not for breeding or seed production.

Still further, the present invention provides a hybrid corn plant produced by growing the harvested seeds produced on the male-sterile plant as well as grain produced by the hybrid corn plant.

A single cross hybrid is produced when two different inbred parent corn plants are crossed to produce first generation $F_1$ hybrid progeny. Generally, each inbred parent corn plant has a genotype which complements the genotype of the other inbred parent. Typically, the $F_1$ progeny are more vigorous then the respective inbred parent corn plants. This hybrid vigor, or heterosis, is manifested in many polygenic traits, including markedly improved yields and improved stalks, roots, uniformity and insect and disease resistance. It is for this reason that single cross $F_1$ hybrids are generally the most sought after hybrid. A three-way, or modified single-cross hybrid is produced from three inbred lines (or synthetics) where two of the inbred lines are crossed (A×B) and then the resulting $F_1$ hybrid is crossed with the third inbred (A×B)×C, as where a modified female is used in the cross. A modified female provides an advantage of improved seed parent yield whereas a modified male improves pollen flow. A double cross hybrid is produced from four inbred lines crossed in pairs (A×B and C×D), thereby resulting in two $F_1$ hybrids that are crossed again. Double cross hybrids are more common in countries wherein less demand exists for higher yielding single cross hybrids. Synthetic populations or crosses are developed by crossing two or more inbred lines (or hybrids, or germplasm sources) together and then employing one of many possible techniques to random mate the progeny. Random mating the progeny is any process used by plant breeders to make a series of crosses that will create a new germplasm pool from which new breeding lines can be derived. Much of the hybrid vigor exhibited by $F_1$ hybrids is lost in the next generation ($F_2$). Consequently, seed from hybrids are not typically used for planting stock.

B. Physical Description of $F_1$ Hybrids and $F_1$ Hybrid Comparison

During the development of a hybrid plant detailed evaluations of the phenotype are made including formal comparisons with other commercially successful hybrids. Because the corn is grown in close proximity, environmental factors that affect gene expression, such as moisture, temperature, sunlight, and pests, are minimized For a decision to be made to commercialize a hybrid, it is not necessary that the hybrid be better than all other hybrids. Rather, significant improvements must be shown in at least some traits that would create improvements in some niches. Examples of such comparative performance data for the hybrid corn plant 980001 (TC1507+ NK603) are set forth herein below in Table 2.

TABLE 2

| Characteristic | Corn Hybrid 980001 | Mycogen 2H697 | Mycogen F2F449 |
| --- | --- | --- | --- |
| Tons @ 65 MST | 23.6 | 27.8 | 22.1 |
| MST % | 65.3 | 62.7 | 63.2 |
| P_SL | 0.1 | 0.2 | 0.0 |
| P_RL | 1.1 | 1.1 | 1.5 |
| PHT (cm) | 263 | 251 | 220 |
| E.H (cm) | 138 | 140 | 104 |
| Starch Mean | 24.3 | 28.7 | 27.8 |
| NDFD % | 71.49 | 59.43 | 70.85 |
| Env | 29 | 29 | 29 |
| Years | 1 | 1 | 1 |
| Population | 25 | 24 | 25 |
| D/TA | 8.3 | 9.7 | 7.7 |

V. Novel 980001-Derived Plants

All plants produced using hybrid corn variety 980001 as a parent are within the scope of this invention. This includes plants essentially derived with the term "essentially derived variety" having the meaning ascribed to such term in 7 U.S.C. §2104(a)(3) of the Plant Variety Protection Act, which definition is hereby incorporated by reference. This also includes progeny plant and parts thereof with at least one ancestor that is hybrid corn variety 980001 and more specifically where the pedigree of this progeny includes 1, 2, 3, 4, and/or 5 or cross pollinations to hybrid corn variety 980001, or a plant that has 980001 as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if 980001 were used in the development of a progeny line, and would also know how many breeding crosses to a line other than 980001 were made in the development of any progeny line. A progeny line so developed may then be used in crosses with other, different, corn inbreds to produce first generation F1 corn hybrid seeds and plants with superior characteristics.

Accordingly, another aspect of the present invention is methods for producing an inbred corn line 980001-derived corn plant. This method for producing a 980001-derived corn plant, comprises: (a) crossing hybrid corn variety 980001 with a second corn plant to yield progeny corn seed; and, (b) growing the progeny corn seed, (under plant growth conditions), to yield the 980001-derived corn plant. Such methods may further comprise the steps of: (c) crossing the 980001-derived corn plant with itself or another corn plant to yield additional 980001-derived progeny corn seed; (b) growing the progeny corn seed of step (d) (under plant growing conditions), to yield additional 980001-derived corn plants; and (e) repeating the crossing and growing steps of (c) and (d) from 0 to 7 times to generate further 980001-derived corn plants. Still further, this may comprise utilizing methods of haploid breeding and plant tissue culture methods to derive progeny of the 980001-derived corn plant.

VI. Corn Transformation

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present invention, in particular embodiments, also relates to transformed versions of the claimed hybrid corn variety 980001 containing one or more transgenes.

Backcrossing methods can be used with the present invention to improve or introduce a trait in a hybrid via modification of its inbred parent(s). The term backcrossing as used herein refers to the repeated crossing of a hybrid progeny back to one of the parental corn plants for that hybrid. The parental corn plant which contributes the locus or loci for the desired trait is termed the nonrecurrent or donor parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol (Poehlman et al., 1995; Fehr, 1987; Sprague and Dudley, 1988).

In a typical backcross protocol, the original parent hybrid of interest (recurrent parent) is crossed to a second variety (nonrecurrent parent) that carries the genetic locus of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the transferred locus from the nonrecurrent parent. The backcross process may be accelerated by the use of genetic markers, such as SSR, RFLP, SNP or AFLP markers to identify plants with the greatest genetic complement from the recurrent parent.

The selection of a suitable recurrent parent is an important step for a successful backcrossing procedure. The goal of a backcross protocol is to add or substitute one or more new traits in the original inbred and hybrid progeny therefrom. To accomplish this, a genetic locus of the recurrent parent is modified or substituted with the desired locus from the nonrecurrent parent, while retaining essentially all of the rest of the desired genetic, and therefore the desired physiological and morphological constitution of the original plant. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, waxy starch, herbicide resistance, resistance for bacterial, fungal, or viral disease, insect resistance, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where a genetic locus acts as a dominant trait. An example of a dominant trait is the herbicide resistance trait. For this selection process, the progeny of the initial cross are sprayed with the herbicide before the backcrossing. The spraying eliminates any plants which do not have the desired herbicide resistance characteristic, and only those plants which have the herbicide resistance gene are used in the subsequent backcross. This process is then repeated for all additional backcross generations.

It is understood to those of skill in the art that a transgene need not be directly transformed into a plant, as techniques for the production of stably transformed corn plants that pass single loci to progeny by Mendelian inheritance is well known in the art. Such loci may therefore be passed from parent plant to progeny plants by standard plant breeding techniques that are well known in the art.

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it should be appreciated by those having ordinary skill in the art that certain changes and modifications such as single gene modifications and mutations, somoclonal variants, variant individuals selected from large populations of the plants of the instant inbred and the like may be practiced within the scope of the invention, as limited only by the scope of the appended claims, without departing from the true concept, spirit, and scope of the invention.

What is claimed is:

1. A seed of the hybrid corn variety 980001, produced by crossing a first plant of variety BE1146BMR with a second plant of variety LLD06BM, wherein representative seed of said varieties BE1146BMR and LLD06BM have been deposited under ATCC Accession numbers PTA-5448 and PTA-8519, respectively.

2. A plant of the hybrid corn variety 980001 grown from the seed of claim 1.

3. A plant part of the plant of claim 2.

4. The seed of claim 1, wherein one or both of the first and second plants further comprises a transgene.

5. The seed of claim 4, wherein the transgene confers a trait selected from the group consisting of male sterility, herbicide tolerance, insect resistance, disease resistance, modified fatty acid metabolism, modified phytic acid metabolism, modified carbohydrate metabolism and modified protein metabolism.

6. The seed of claim 4, wherein the first and second plants each comprise a different transgene.

7. The seed of claim 1, wherein one or both of the first and second plants comprises a single locus conversion.

8. The seed of claim 7, wherein the single locus conversion confers a trait selected from the group consisting of male sterility, herbicide tolerance, insect resistance, disease resistance, modified fatty acid metabolism, modified phytic acid metabolism, modified carbohydrate metabolism and modified protein metabolism.

9. A method of producing hybrid corn seed comprising crossing a plant of variety BE1146BMR with a plant of variety LLD06BM, wherein representative seed of variety BE1146BMR and variety LLD06BM have been deposited under ATCC Accession numbers PTA-5448 and PTA-8519, respectively.

10. The method of claim 9, defined as comprising pollinating a plant of inbred variety BE1146BMR with pollen from a plant of variety LLD06BM.

11. The method for producing corn grain comprising growing the plant of claim 2 until grain is produced and collecting the grain.

12. A method of introducing a heritable trait into hybrid corn variety 980001 comprising the steps of:
    (a) crossing a first plant of a first inbred corn variety selected from the group consisting of variety BE1146BMR and variety LLD06BM with another corn plant that heritably carries the trait to produce progeny plants, at least some of which heritably carry the trait, wherein representative samples of seed of variety BE1146BMR and variety LLD06BM have been deposited under ATCC Accession numbers PTA-5448 and PTA-8519, respectively;
    (b) selecting progeny plants that heritably carry the trait;
    (c) crossing selected progeny plants with another plant of the first inbred corn variety to produce next-generation progeny plants at least some of which heritably carry the trait;
    (d) selecting next-generation progeny plants that heritably carry the trait and exhibit morphological and physiological characteristics of the first inbred corn variety;
    (e) repeating steps (c) and (d) three or more times to produce at least a first selected progeny plant that heritably carries the trait and exhibits essentially all of the morphological and physical characteristics of the inbred corn variety; and
    (f) crossing a progeny plant of step (e) with a plant of the other inbred corn variety of the group consisting of BE1146BMR and LLD06BM, having been deposited under ATCC Accession numbers PTA-5448 and PTA-8519, respectively to produce a plant comprising the trait and essentially all of the characteristics of hybrid corn variety 980001 when grown under the same environmental conditions.

13. The method of claim 12, wherein the trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

14. The method of claim 13, further comprising repeating steps (a)-(f) at least once to introduce at least a second trait into hybrid corn variety 980001, wherein the second trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

15. A plant produced by the method of claim 12.

16. A method of introducing a desired trait into hybrid corn variety 980001 comprising the steps of:
    (a) introducing a transgene conferring the trait into a variety selected from the group consisting of BE1146BMR and LLD06BM, having been deposited under ATCC Accession numbers PTA-5448 and PTA-8519, respectively, to produce a transgenic plant heritably carrying the trait; and
    (b) crossing the transgenic plant or an isogenic progeny plant thereof with a plant of the other inbred corn variety to produce seed of the hybrid corn variety 980001 that heritably carries and expresses the transgene and otherwise has essentially all of the morphological and physiological characteristics of hybrid corn variety 980001 when grown under the same environmental conditions.

17. The method of claim 16, wherein the desired trait selected from the group consisting of male sterility, herbicide tolerance, insect resistance, disease resistance, waxy starch, modified fatty acid metabolism, modified phytic acid metabolism, modified carbohydrate metabolism and modified protein metabolism.

18. The method of claim 16, further comprising repeating steps (a) and (b) at least once to introduce at least a second trait into hybrid corn variety 980001, wherein the second trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

19. A plant produced by the method of claim 18.

20. A method of producing a corn plant derived from the hybrid corn variety 980001, comprising crossing the plant of claim 2 with a second corn plant to produce a progeny corn plant derived from the hybrid corn variety 980001.

\* \* \* \* \*